United States Patent [19]

Knoch et al.

[11] Patent Number: 5,575,282

[45] Date of Patent: Nov. 19, 1996

[54] OXYGEN DISTRIBUTOR WITH BOTH MOUTH AND NOSE DELIVERY PORTS

[75] Inventors: Martin Knoch, Berg; Dieter Kohler, Winkhausen; Matthias Remke, Starnberg, all of Germany

[73] Assignee: Paul Ritzau Pari-Werk GmbH, Starnberg, Germany

[21] Appl. No.: 333,613

[22] Filed: Nov. 1, 1994

Related U.S. Application Data

[63] Continuation of Ser. No. 148,410, Nov. 8, 1993, abandoned, which is a continuation of Ser. No. 837,403, Feb. 18, 1992, abandoned.

[30] Foreign Application Priority Data

Feb. 22, 1991 [DE] Germany .......................... 41 05 672.8

[51] Int. Cl.$^6$ .......................... A61M 16/00; A61M 15/08; A62B 9/06; A62B 7/00

[52] U.S. Cl. .................. 128/204.18; 128/205.11; 128/207.14; 128/207.18; 128/912; 128/207.17

[58] Field of Search .................. 128/204.18, 206.25, 128/207.14, 207.17, 207.18, 912, DIG. 26, 205.11

[56] References Cited

U.S. PATENT DOCUMENTS

| | | | |
|---|---|---|---|
| 3,209,755 | 10/1965 | McCarthy | 128/348 |
| 3,513,844 | 5/1970 | Smith | 128/206 |
| 3,648,703 | 3/1972 | Manker | 128/348 |
| 3,726,275 | 4/1973 | Jackson | 128/206 |
| 3,802,431 | 4/1974 | Farr | 128/206 |
| 4,018,221 | 4/1977 | Rennie | 128/185 |
| 4,106,505 | 8/1978 | Salter | 128/206 |
| 4,156,426 | 5/1979 | Gold | 128/205 |
| 4,263,908 | 4/1981 | Mizerak | 128/207.18 |
| 4,266,540 | 5/1981 | Panzik | 128/207.13 |
| 4,278,082 | 7/1981 | Blackmer | 128/207.18 |
| 4,354,488 | 10/1982 | Bartos | 128/205.25 |
| 4,406,283 | 9/1983 | Bir | 128/DIG. 26 |
| 4,454,880 | 6/1984 | Muto et al. | 128/207.18 |
| 4,739,757 | 4/1988 | Edwards | 128/DIG. 26 |
| 5,273,032 | 12/1993 | Borody | 128/207.14 |

FOREIGN PATENT DOCUMENTS

| | | |
|---|---|---|
| 2445720 | 8/1980 | France . |
| 3215466 | 3/1984 | Germany . |
| 3821687 | 1/1990 | Germany . |
| 8703704 | 6/1987 | WIPO . |

*Primary Examiner*—Kimberly L. Asher
*Attorney, Agent, or Firm*—Merchant, Gould, Smith, Edell, Welter & Schmidt, P.A.

[57] ABSTRACT

In oxygen therapy, the patient is provided a mixture of air and oxygen. In the process, the oxygen is led from an oxygen supply container or an oxygen concentrator through a tube to the patient and made available for inhalation. The distribution system includes a whirler with openings directed toward the patient's mouth and nose. The oxygen flow is twisted into a spiral shape inside the whirler before it exits from the openings.

16 Claims, 1 Drawing Sheet

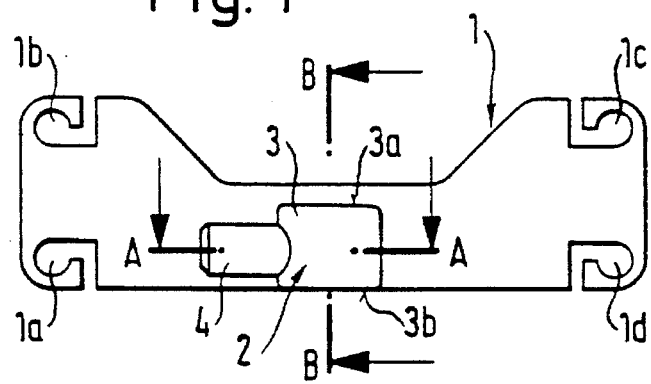
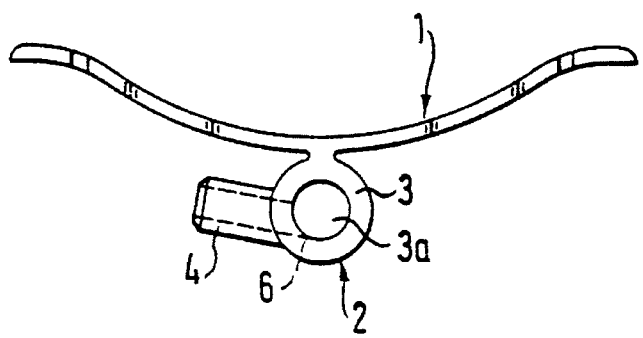
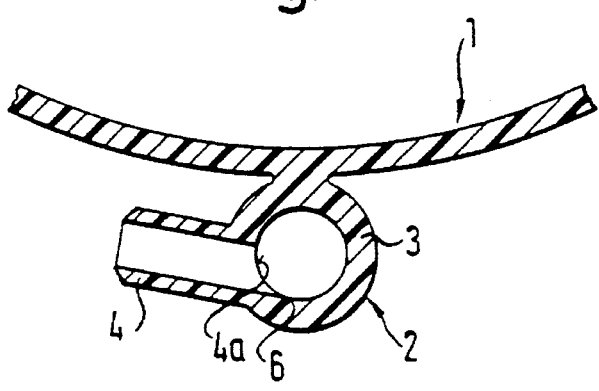
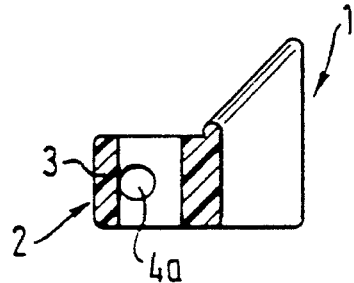

OXYGEN DISTRIBUTOR WITH BOTH MOUTH AND NOSE DELIVERY PORTS

This application is a continuation of U.S. application Ser. No. 08/148,810 filed Nov. 8, 1993, now abandoned which is a continuation of Ser. No. 07/837,403 filed Feb. 18, 1992 now abandoned.

FIELD OF THE INVENTION

The invention refers to an oxygen distributor for use in oxygen therapy for patient treatment.

BACKGROUND OF THE INVENTION

In oxygen therapy, the patient is provided with a mixture of air and oxygen. In the process, the oxygen is led from an oxygen supply container through a tube to the patient and made available for inhalation. For this, the oxygen led to the mouth and nose area through known distributor systems is fed to one or both sides of the nose. These distributor systems are generally designed in such a way that they consist of combined tubing sections and have either one or two short tubing elements that reach into the wings of the nose and from the open ends of which the oxygen flows out.

In oxygen therapy, output volumes of 2 to 5 liters per minute are attained, in such a way as to produce flow rates of up to 660 cm/s for one discharge opening and 330 cm/s for two discharge openings, with an average inside diameter of approximately 4 mm for the discharge point of the tubing elements. Correspondingly greater values result from smaller diameters (2 to 3 mm). These flow rates are so high that it can be extremely uncomfortable for the patient. Attempts have therefore been made to reduce the speed of the oxygen flowing out.

U.S. Pat. No. 3,802,431 proposed to design the tubing elements led into the nose openings in such a way that they widen in a funnel shape and the oxygen flow runs from the smaller diameter to the larger diameter. This reduces the flow rate, resulting in an administration of oxygen that is more comfortable for the patient.

In most distributor systems the oxygen is led into the wings of the nose through the aforementioned tubing elements. Oxygen is supplied in sufficient quantity in this way as long as the patient breathes through the nose, and the oxygen can be dosed quite precisely. However, only an insufficient quantity of oxygen is guaranteed if the patient breathes through the mouth.

To guarantee oxygen administration at least to a limited extent when the patient breathes through the mouth, U.S. Pat. No. 4,156,426 proposes to complete the distributor system with an opening to the mouth, through which the oxygen fed to the distributor system can also exit. In this distributor system the main supply is still provided through two tubing elements sticking into the nasal cavities. When the patient inhales through the nose, both the supplied oxygen and the ambient air through the additional opening are led into the nasal cavities. When the patient exhales through the nose or inhales through the mouth, the oxygen flows out through the additional opening and makes its way into the patient's open mouth in such a way that oxygen is fed to the patient in this way. When the distributor system is designed like this, however, there is a considerable difference in oxygen dosing between inhaling through the nose and inhaling through the mouth. The additional opening of the distributor system directed to the mouth releases the oxygen diffusely, particularly when the patient exhales through the nose. Oxygen is thus supplied in clearly lower amounts when the patient inhales through the mouth, in such a way that the total dose can no longer be determined in a reliable manner since it depends on how often the patient has inhaled through the nose or through the mouth.

All distributor systems with tubing elements that reach into the inside of the nose have in common that they are not very comfortable to wear and are experienced as burdensome by the patient. Even soft plastics, such as those in U.S. Pat. No. 3,802,431 do not provide impairment-free wearing of the oxygen distributor systems. Padding the tubing elements inside the nose is only feasible to a limited extent and always leads to complete closing of the nose, in such a way that the patient has no choice but to exhale through the mouth.

SUMMARY OF THE INVENTION

The present invention provides a distributor, particularly for use in oxygen therapy for patient treatment, in which the patient is provided with oxygen in a comfortable manner and which guarantees reliable oxygen provision with good dosing ability when the patient inhales through the nose as well when the patient inhales through the mouth.

BRIEF DESCRIPTION OF THE DRAWINGS

FIG. 1 a front view of a form of construction of the oxygen distributor according to the invention, FIG. 2 a top view of the form of construction of FIG. 1, FIG. 3 a cross-section view along line A in FIG. 1, and FIG. 4 a cross-section view along line B in FIG. 1.

DESCRIPTION OF THE PREFERRED EMBODIMENT

The form of construction illustrated in FIG. 1 of an oxygen distributor according to the invention includes a basic body 1 and a distributor element 2. The basic body 1 bears the distributor element 2 and also serves to support and position the entire oxygen distributor between the patient's nose and upper lip. For this, the basic body has laterally arranged loops 1a–1d into which an adjustable strap (not shown) can be inserted, placed around the patient's head and pulled tight to fasten the oxygen distributor.

The distributor element 2 includes a whirler 3 in the form of an initial short tubing element the longitudinal axis of which runs vertically, as shown in the drawing, in such a way that the two open ends 3a and 3b of the whirler are arranged toward the patient's nose and mouth when the oxygen distributor is worn. In the form of construction illustrated, the whirler has a constant cross-section over its entire length and thus encloses a cylindrical cavity or passage in its interior. For the diameter of the cylindrical tubing element, values of 4 to 8 mm have proven particularly effective. The length of the tubing element is preferably from 1.5 to 2 times its diameter.

The oxygen is fed through a tube (not shown in the illustration) that is attached to the free end of connecting piece 4 and can be secured on the straps or on the basic body 1. In the form of construction illustrated, the connecting piece 4 is also a short tubing element having a passage, the longitudinal axis of which runs vertically to the longitudinal axis of the whirler 3 and which has a smaller diameter than the whirler 3, preferably 0.3 to 0.5 times the diameter of the whirler (2 to 4 mm), and of constant cross section. As FIG. 1 shows, the connecting piece 4 is arranged halfway up the whirler 3. As FIG. 2 shows, the longitudinal axes of the whirler 3 and of the connecting piece 4 are not on one level. On the contrary, as FIG. 4 shows, the opening 4a formed by the connecting piece 4 in the inner wall of the whirler 3 is staggered in relation to the longitudinal axis of the whirler. A particularly advantageous design, as FIG. 3 shows, has the inner wall of the connection piece 4 continuing in area 6 without transition into the inner wall of the whirler 3 i.e. connecting piece 4 is oriented tangentially with respect to whirler 3.

If oxygen is fed through the connection piece 4, it exits from the opening 4a and makes its way into the cylindrical interior of the whirler 3. The oxygen flow, straight at first, is deflected at this point, leading to a spiral oxygen flow that runs to the two open ends of the whirler 3. The deflection and whirling, as well as the transition to a larger cross-section, slow the oxygen flow in such a way that the patient no longer finds it uncomfortable when the oxygen exits from the open end of the whirler 3. At standstill, i.e., with no breathing taking place, essentially equal volumes come out at both ends of the whirler 3, each corresponding to about half the volume of oxygen supplied.

The spiral oxygen flow forming in the whirler 3 is unstable, however, in such a way that when the patient inhales, nearly the entire volume of oxygen is deflected, in such a way that it exits at one of the open ends of the whirler 3. Starting with the conditions shown in FIG. 1, the spirally whirled oxygen flow is deflected upward when the patient inhales through the nose, while there is a downward deflection when the patient inhales through the mouth.

The centrifugal force at work during whirling breaks the whirl after it exits the whirler 3, thus compelling the flow rates to slow down quickly and the oxygen to mix thoroughly with the surrounding air. Because of the design of the whirler 3, neither of the two openings is given more oxygen, but rather the oxygen flow is determined solely by the inhalation process. This means that there is a largely uniform supply of oxygen whether the patient inhales through the nose or through the mouth.

As for exhaling, only exhaling through the nose has a disruptive effect on the oxygen flow formed in the whirler 3. The aforementioned high outflow rates at the opening 4a lead to rapid restoration of a spirally whirled oxygen flow in the oxygen distributor according to the invention. This oxygen flow exits from both ends 3a and 3b of the whirler 3 in nearly equal portions.

In spite of the large exit surface at the two open ends 3a and 3b of the whirler, the whirling of the oxygen flow inside the whirler 3 also causes a sufficiently well aimed oxygen flow to occur, promoting oxygen administration during inhalation.

To make the oxygen distributor more comfortable to wear, as FIGS. 2 and 3 show, the basic body 1 of the form of construction is not designed level but curved and with a radius that adapts to the anatomical features of the human face. The distributor element 2, consisting of the whirler 3 and the connection piece 4, which are arranged essentially at right angles to one another, is staggered in relation to the basic body in such a way that the longitudinal axis of the connection piece 4 runs essentially parallel to the part of the surface of the basic body 1 that is immediately adjacent to the point of attachment of the distributor element 2 to the basic body 1. This slightly distorted arrangement as shown in FIGS. 2 and 3 facilitates the connection of the hose supplying the oxygen, particularly with regard to support when the patient is wearing it.

A virtually level basic body 1 of the oxygen distributor according to the invention can be made from a plastically deformable material in such a way that the oxygen distributor can be adapted to the contours of the patient's face when the distributor is put on. Elastic materials can be plastically stiffened by a core in such a way that the basic body can be plastically deformed even if the basic body material has no plastic characteristics. With this design, it is possible to choose the material only on the basis of how tolerable it is and how comfortable it is to wear, without the plastic requirements restricting the possible choice of materials.

As FIG. 3 shows, the form of construction described involves a one-piece plastic body that can be manufactured with the die-casting process. Neither the whirler 3 nor the connection piece 4 require a particular design of the surfaces in the area where the oxygen flows. Therefore, particular consideration can be given to compatibility and wearing comfort as well as economical production when designing and choosing materials.

In the forms of construction illustrated, the oxygen distributor according to the invention weighs very little, further improving wearing comfort. Hindering the patient when speaking or eating is thus avoided. Furthermore, since the oxygen is provided in a sufficiently well aimed flow and is always inhaled along with the ambient air, the patient can still smell things, in however limited manner, during the oxygen therapy.

We claim:

1. An oxygen distributor for use in oxygen therapy, said distributor comprising:
    a basic body which positions the oxygen distributor in the area between the patient's mouth and nose;
    a connecting element for connecting an oxygen feed; and
    a whirler encompassing a whirling space that has end openings oriented toward the patient's mouth and nose and into which the connecting element leads, the orientation of the end openings of the whirler, its interior size relative to that of the connecting element, and the configuration of the intersection of the connecting element to the whirler spirally whirling oxygen flow fed through the connecting element and forming an unstable spiral oxygen flow, wherein oxygen exits essentially equally from both openings of the whirler at standstill and mixes with ambient air.

2. An oxygen distributor according to claim 1, wherein the whirler has a larger cross-sectional area than the connecting element.

3. An oxygen distributor according to claim 1, wherein the whirler is an initial short tubing element and the connecting element is a second short tubing element the longitudinal axis of which runs vertically to, and not level with, the longitudinal axis of the first tubing element.

4. An oxygen distributor according to claim 3, wherein the two tubing elements have a constant cross-section.

5. An oxygen distributor according to claim 3, wherein the two tubing elements have a circular cross-section.

6. An oxygen distributor according to claim 1, wherein the whirler is formed integrally with the connecting element.

7. An oxygen distributor according to claim 1, wherein the basic body is formed integrally with the whirler.

8. An oxygen distributor according to claim 1, wherein the basic body has loops to accommodate a strap for attaching to the patient's head.

9. An oxygen distributor according to claim 1, wherein the basic body is curved to fit the user's face.

10. An oxygen distributor according to claim 1, wherein the basic body is made of a plastically deformable material.

11. An oxygen distributor according to claim 10, wherein the basic body has a plastically deformable core.

12. An oxygen distributor according to claim 1, wherein the basic body, the whirler and the connecting element are made of plastic.

13. An oxygen distributor for use in oxygen therapy, said distributor comprising:

a basic body which positions the oxygen distributor in the area between the patient's mouth and nose;

a connecting element for connecting an oxygen feed;

a whirler encompassing a whirling space that has openings toward the patient's mouth and nose and into which the connecting element leads, in such a way that the oxygen flow fed through the connecting element is spirally whirled and exits from both openings of the whirler at standstill, wherein the whirler is an initial short tubing element and the connecting element is a second short tubing element the longitudinal axis of which runs vertically to, and not level with, the longitudinal axis of the first tubing element; and wherein the tubing element forming the connecting element runs tangentially into the tubing element forming the whirler.

14. An oxygen distributor for use in oxygen therapy, comprising:

a basic body having a shape and size so as to permit the basic body to be positioned in use on a user's face in an area between the mouth and nose;

a first tubular element mounted on the basic body, having a sidewall defining a central opening and having opposed open first and second ends which in use are oriented toward a user's nose and mouth respectively; and a second tubular member having a first end which joins the sidewall of the first tubular element intermediate the open first and second ends, the second tubular member having a sidewall which defines a central passage, the central passage of the second tubular member running into the central passage of the first tubular member, the second tubular member having an open second end which is adapted for connection to an oxygen feed, the passage of the second tubular member being smaller in diameter than that of the first tubular member.

15. The oxygen distributor of claim 14, wherein the first and second tubular members have a circular and constant cross section.

16. The oxygen distributor of claim 15, wherein the opening of the second tubular member is oriented tangentially with respect to the opening of the first tubular member.

* * * * *